(12) United States Patent
Wang et al.

(10) Patent No.: US 12,304,923 B2
(45) Date of Patent: May 20, 2025

(54) USE OF IONIZATION RADIATION SOURCE IN PREPARATION OF POROUS CRYSTALLINE MATERIAL

(71) Applicant: SOOCHOW UNIVERSITY, Suzhou (CN)

(72) Inventors: Shuao Wang, Suzhou (CN); Mingxing Zhang, Suzhou (CN); Junchang Chen, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 833 days.

(21) Appl. No.: 17/424,870

(22) PCT Filed: Apr. 27, 2020

(86) PCT No.: PCT/CN2020/087265
§ 371 (c)(1),
(2) Date: Jul. 21, 2021

(87) PCT Pub. No.: WO2021/212532
PCT Pub. Date: Oct. 28, 2021

(65) Prior Publication Data
US 2022/0315610 A1    Oct. 6, 2022

(30) Foreign Application Priority Data
Apr. 24, 2020   (CN) .......................... 202010333538.X

(51) Int. Cl.
*C07D 251/24*    (2006.01)
*C07F 7/00*     (2006.01)

(52) U.S. Cl.
CPC ............ *C07F 7/003* (2013.01); *C07D 251/24* (2013.01)

(58) Field of Classification Search
CPC ...................................................... C07F 7/003
See application file for complete search history.

(56) References Cited

FOREIGN PATENT DOCUMENTS

| CN | 102190797 A | 9/2011 | |
|----|-------------|--------|---|
| CN | 104138746 A | 11/2014 | |
| CN | 104667876 A | 6/2015 | |
| CN | 105385965 A | 3/2016 | |
| CN | 106674534 A | 5/2017 | |
| CN | 110252410   | * 7/2019 | ............. C01B 3/042 |
| CN | 110156039 A | 8/2019 | |
| CN | 110252410 A | 9/2019 | |
| EP | 2846896 A1  | 3/2015 | |

OTHER PUBLICATIONS

Tanase et.al (ACS Catal. 2016, 6, 6063-6072) (Year: 2016).*

* cited by examiner

*Primary Examiner* — John S Kenyon
*Assistant Examiner* — Rehana Ismail
(74) *Attorney, Agent, or Firm* — SZDC Law PC

(57) ABSTRACT

The present invention provides use of an ionization radiation source in preparation of a porous crystalline material, and a method for preparing a MOFs material and a COFs material. In the present invention, the ionization radiation source is used for preparing the porous crystalline material; under the irradiation of the ionization radiation source, the porous crystalline material (MOFs, COFs) can be synthesized in an extremely short time, wherein the ionization radiation source is used for providing energy required in a reaction for preparing the porous crystalline material. The preparation process does not need heating, so that energy consumption is reduced and a high-pressure system is avoided. The aforementioned preparation method is simple, low in instrument and equipment cost, and thus is a environmentally friendly and extremely low-cost synthesis method.

19 Claims, 8 Drawing Sheets

USE OF IONIZATION RADIATION SOURCE IN PREPARATION OF POROUS CRYSTALLINE MATERIAL

This application is the National Stage Application of PCT/CN2020/087265, filed on Apr. 27, 2020, which claims priority to Chinese Patent Application No. 202010333538.X, filed on Apr. 24, 2020, which is incorporated by reference for all purposes as if fully set forth herein.

FIELD OF THE INVENTION

The present invention relates to the technical field of porous crystalline materials, and more particularly to use of an ionization radiation source in preparation of a porous crystalline material.

DESCRIPTION OF THE RELATED ART

Porous crystalline materials mainly include metal organic frameworks (MOFs) and covalent organic frameworks (COFs). The metal organic frameworks (MOFs) are organic-inorganic hybrid crystalline materials with intramolecular pores formed by self-assembly of organic ligands and metal ions or clusters through coordination bonds. Compared with other crystalline polymer materials, the MOFs have excellent properties such as porosity, large specific surface area, structural diversity, functional diversity and unsaturated metal sites. The covalent organic frameworks (COFs) is a kind of crystalline organic polymer materials that are composed of light atoms such as C, H, B, O, N, etc., and formed by connecting organic units through chemical covalent bonds. Compared with other crystalline polymer materials, the COFs have excellent properties such as low density, porosity, pore adjustability, high thermal stability and chemical stability. Since the novel porous crystalline materials (MOFs and COFs) were first reported, great progress of such materials have been made in many application fields, including gas storage, separation and purification, heterogeneous catalysis, photoelectric conversion, proton conduction, energy storage, detection, fluorescence, drug delivery and so on.

Traditional methods for synthesizing novel porous crystalline materials (MOFs and COFs) are mainly solvothermal methods, that is, precursors for synthesizing a porous crystalline material (MOFs, COFs) are pre-dispersed in an organic solvent, then the reaction system is sealed, and then subjected to nucleation, growth, crystallization, error repair, structural rearrangement and the like at a certain temperature and autogenous pressure, so as to form the porous crystalline material. The novel porous crystalline material (MOFs and COFs) prepared by this method has good crystallinity, but the reaction needs to be carried out in a high-temperature sealed system, and vapor pressure will be generated in the reaction process, so that the method has high requirements for reaction equipment, long synthesis time, and low yield, and thus is not suitable for large-scale production and is difficult to realize industrial production, thereby limiting the potential application of the material in industry.

In order to overcome the shortcomings mentioned above, many other preparation methods have been successively used for preparing novel porous crystalline materials (MOFs, COFs), including an ionothermal synthesis method, a microwave-assisted method, a mechanical grinding method, and the like. The ionothermal synthesis method replaces the organic solvent with an ionic liquid or a fused salt, which avoids the generation of high pressure in the reaction process, but still not overcomes the shortcomings of high temperature, long time and low yield. The microwave-assisted method uses microwave energy to promote the formation of novel porous crystalline materials (MOFs, COFs) and greatly shorten the reaction time, but the reaction system still has shortcomings such as high temperature and high pressure. The mechanical grinding method accelerates the formation of novel porous crystalline materials (MOFs, COFs) under room temperature and normal pressure, but the prepared materials have poor crystallinity and low specific surface area. Therefore, it is still necessary to explore efficient, rapid and environmentally friendly methods for preparing novel porous crystalline materials (MOFs and COFs) continually.

SUMMARY OF THE INVENTION

In order to solve the aforementioned technical problems, an object of the present invention is to provide use of an ionization radiation source in preparation of a porous crystalline material. In the present invention, the ionization radiation source is used for preparing the porous crystalline material, wherein under the irradiation of the ionization radiation source, the porous crystalline material (MOFs, COFs) can be synthesized in an extremely short time. The preparation process does not need heating, so that energy consumption is reduced and a high-pressure system is avoided. The aforementioned preparation method is simple, low in instrument and equipment cost, and thus is environmentally friendly and extremely low-cost.

The first object of the present disclosure is to disclose use of an radiation source in preparation of a porous crystalline material, wherein the ionization radiation source is used for providing energy required in a reaction for preparing the porous crystalline material, and porous crystalline material is a MOFs material or a COFs material.

Preferably, the reaction for preparing the porous crystalline material is carried out at 20-30° C. under normal pressure.

Preferably, the ionization radiation source is selected from the group consisting of an electron beam, gamma-ray radiation, proton beam, helium ion beam and any combination thereof.

Preferably, the irradiation dose of the ionization radiation source is 5-3,000 kGy. More preferably, the irradiation dose of the ionization radiation source is 50-1,000 kGy.

Preferably, the irradiation time of the ionization radiation source is 8 s-100 h. More preferably, the irradiation time of the ionization radiation source is less than 17 hours.

Preferably, the MOFs material includes an inorganic metal center and an organic ligand connected with the inorganic metal center through a coordination bond, wherein the inorganic metal center is selected from transition metal ions such as zinc ions, zirconium ions, copper ions and cobalt ions, and lanthanide and actinide metal ions and any combination thereof; and the organic ligand is derived from imidazole ligands such as 2-methylimidazole, terephthalic acid, trimesic acid and 4,4'-bipyridine, carboxylic acid ligands and pyridine ligands.

Preferably, the MOFs material includes ZIF-8 or UiO-66.

Preferably, the COFs material includes a light element and an organic structural unit connected with the light element through a covalent bond, wherein the light element is selected from C, H, B, O, N atoms and any combination thereof, and the organic structural unit is selected from a conjugated structure such as benzene, pyrene, biphenyl, pyrazine, pyridine and bipyridine.

Preferably, the COFs material includes EB-COF-1 or EB-COF-2, and the structural formulas of EB-COF-1 and EB-COF-2 are sequentially as shown below:

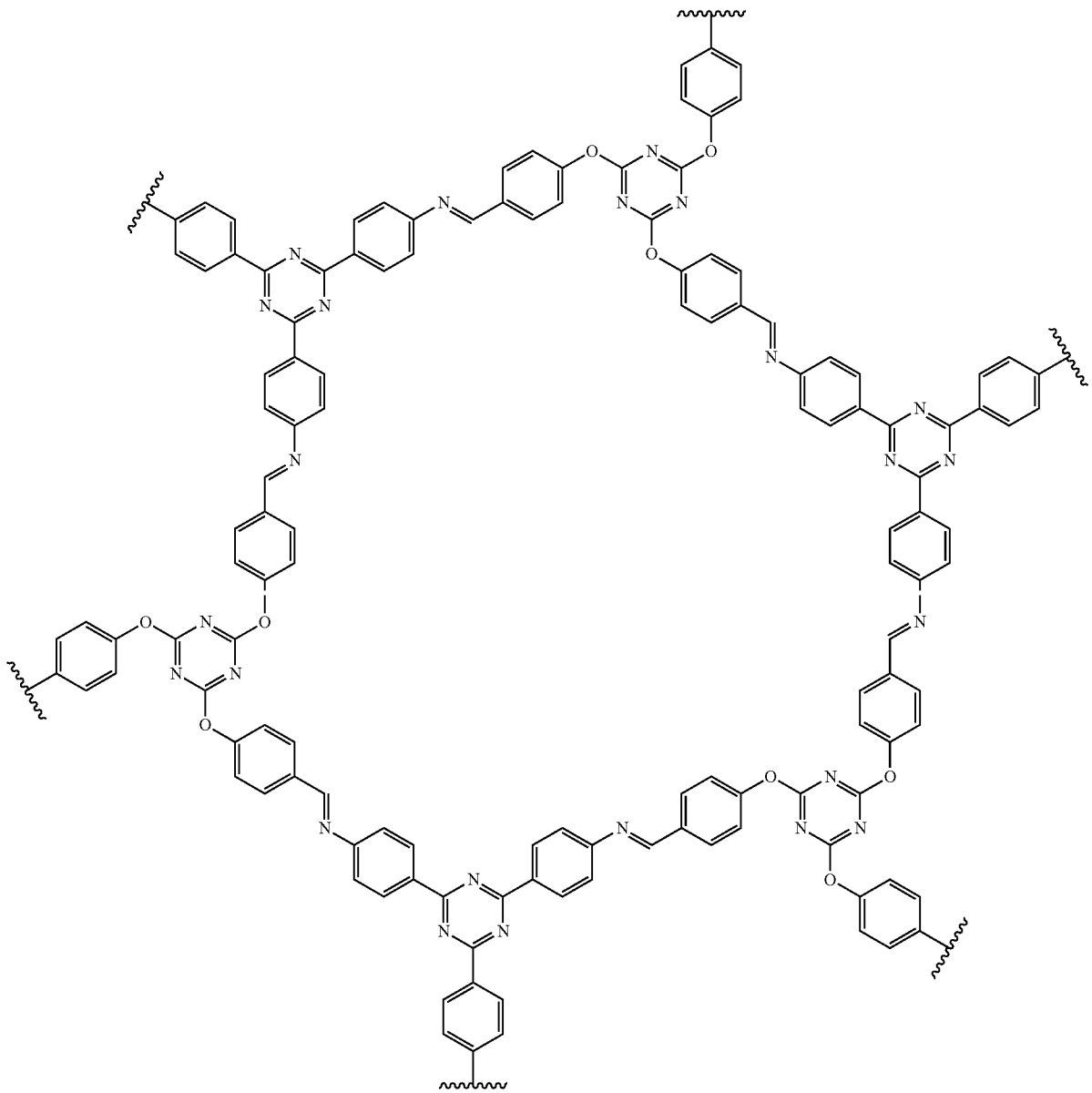

-continued

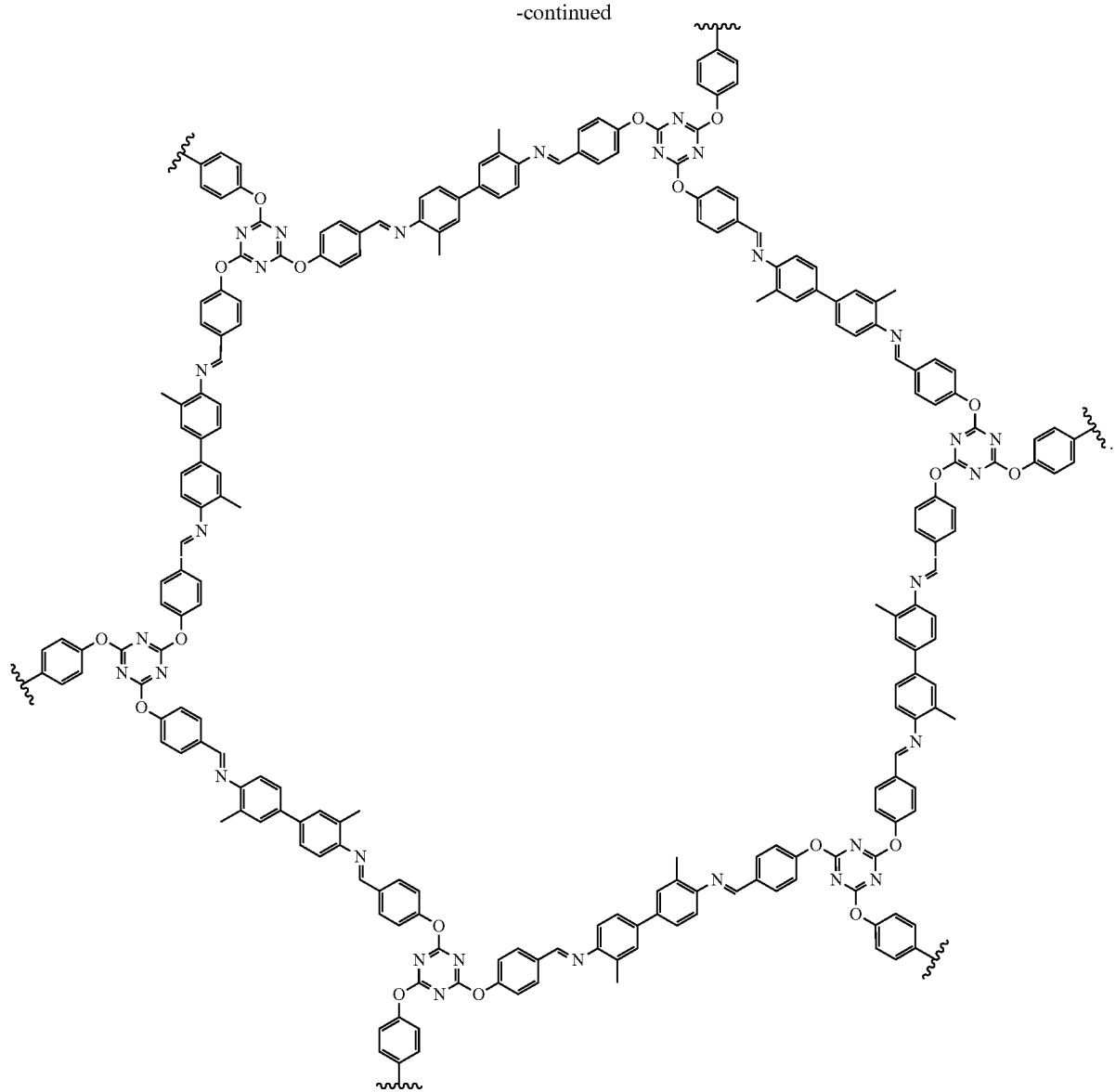

A second object of the present disclosure is to provide a method for preparing a MOFs material, including the steps of:
  dissolving a metal salt and an organic ligand in an organic solvent to obtain a mixed solution; and then irradiating the mixed solution with an ionization radiation source at 20-30° C. under normal pressure until the reaction is complete, to obtain the MOFs material.

Preferably, the ionization radiation source has a irradiation dose of 5-3,000 kGy, and a irradiation time of 8 s-100 h. More preferably, the ionization radiation source has a irradiation dose of 50-1,000 kGy, and a irradiation time less than 17 hours.

More preferably, that metal salt is selected from transition metal salts such as zinc salts, zirconium salts, copper salts, cobalt salts, and lanthanide metal salts and actinide metal salts.

Preferably, the organic ligand is selected from imidazole, carboxylic acid and pyridine ligands, such as 2-methylimidazole, terephthalic acid, trimesic acid and 4,4'-bipyridine.

Preferably, the organic solvent is selected from organic solvents commonly used for synthesizing MOFs materials, such as N,N'-dimethylformamide, n-butanol and 1,2-o-dichlorobenzene.

A third object of the present disclosure is to provide a method for preparing a COFs material, including the steps of:
  under an oxygen-free condition, dissolving organic monomers for synthesizing the COFs material in an organic solvent and acetic acid to obtain a mixed solution; and then irradiating the mixed solution with an ionization radiation source at 20-30° C. under normal pressure until the reaction is complete, to obtain the MOFs material.

Preferably, the ionization radiation source has an irradiation dose of 5-3,000 kGy, and an irradiation time of 8 s-100 h. More preferably, the ionization radiation source has a irradiation dose of 50-1,000 kGy, and an irradiation time less than 17 hours.

Preferably, the organic monomer is selected from organic amines and aldehyde ligands, such as 2,4,6-tris(4-formylphenoxy)-1,3,5-triazine, 2,4,6-tris(4-amino-phenyl)-1,3,5-triazine, 3,3'-dimethylbenzidine, terephthalaldehyde, biphenyldicarbaldehyde, trimesaldehyde, 1,3,5-trihydroxy-2,4,6-trimesaldehyde, 2,5-dihydroxy-terephthalaldehyde, 2,5-dimethoxyterephthalaldehyde, 2,5-bipyridine dicarbaldehyde, p-phenylenediamine, biphenyldiamine, 3,3'-dihydroxybiphenyl diamine, 3,3'-dimethoxybiphenyl diamine and 3,3'-dimethylbiphenyl diamine.

Preferably, the organic solvent is selected from organic solvents commonly used for synthesizing MOFs materials, such as N,N'-dimethylformamide, n-butanol, and 1,2-o-dichlorobenzene.

The methods for preparing the MOFs material and the COFs material according to the present invention does not need high-pressure sealed reactors, and a glass container sealed at normal pressure can be used.

By means of the above technical solution, the present invention has the following advantages:

The present invention provides a brand-new method for preparing a porous crystalline material based on radiation synthesis chemistry. From the perspective of energy supply, it is a simple and very low-cost way to use radiation energy instead of traditional thermal energy. Although the ionization radiation source can be used for providing the heat source required in the reaction process, it is thought that it will destroy the structure of crystalline products in the synthesis of crystalline materials, thereby obtaining amorphous products. In the present invention, the ionization radiation source is creatively used for preparing the porous crystalline material, and the preparation process of the porous crystalline material depends on the interaction between ionizing radiation and substances, so that the radiant energy is converted into the energy required in the reaction system and used for synthesizing the novel porous crystalline materials (MOFs and COFs).

The method for preparing a novel porous crystalline material (MOFs and COFs) of the present invention has the advantages such as simple operation, fast crystallization of products, extremely short synthesis time, no need of heating in the reaction process, low energy consumption, normal pressure condition of the whole reaction system, avoidance of high pressure system and low requirements on reaction vessels. Under the irradiation of an electron beam, the MOFs material can be prepared within 30 minutes, and the COFs material can be prepared within 160 seconds. UiO-66 can be prepared within 17 hours under gamma-ray irradiation.

The method of the present invention can quickly prepare the novel porous crystalline material (MOFs and COFs) at room temperature, and the synthesized porous crystalline material (MOFs and COFs) has excellent crystallinity under a proper absorption dose. Compared with the traditional solvothermal method, the synthesis period is greatly improved, the synthesis time is greatly shortened, no heating is needed in the reaction process, the energy consumption is greatly reduced, and a high-pressure system is avoided; the reaction container does not need to be a sealed reaction device, a simple glass container can be used, thereby reducing the requirements on reaction equipment; and the method of the present invention can realize continuous and rapid preparation of the porous crystalline material (MOFs and COFs), and thus is suitable for industrial production.

The above description is only an overview of the technical solution of the present invention. In order to understand the technical means of the present disclosure more clearly and implement them according to the specification, the following description is made with the preferred embodiments of the present invention in conjunction with the detailed drawings.

DETAILED DESCRIPTION OF THE PREFERRED EMBODIMENTS

In the present invention, a method for synthesizing metal-organic frameworks (MOFs) is as follows.

A certain amount of an organic ligand and a metal salt are accurately weighed in proportion into a 20 mL scintillation flask, added with a certain volume of an organic solvent, and subjected to ultrasonic treatment until the organic ligand and the metal salt are dissolved. The prepared sample is irradiated with an electron beam or gamma-ray for a certain time, and then taken out. The irradiated solid is washed with a suitable organic solvent, and the washed solid product is air-dried at room temperature.

A method for synthesizing covalent organic frameworks (COFs) is as follows.

A certain amount of a monomer is accurately weighed in proportion into a 20 mL scintillation flask, added with a certain volume of an organic solvent and an acetic acid solution, subjected to ultrasonic treatment for 1 minute, then introduced with nitrogen for 4 minutes, and sealed. The sealed sample is irradiated under an electron accelerator for 160 seconds, and then taken out, and the absorption dose is 100 kGy. The solid produced after irradiation is washed twice with tetrahydrofuran and once with absolute ethanol, and the finally obtained solid product is dried in a 60° C. oven.

The chemical structure of the porous crystalline product synthesized by the present invention is determined by Fourier Transform Infrared Spectrometer (FT-IR), and the crystal structure is determined by Powder X-ray Diffraction (PXRD).

The Detailed Description of the present invention will be further described in detail with reference to examples. The following examples are intended to illustrate the present invention, instead of limiting the scope of the present invention.

Unless otherwise specified, the following examples of the present invention are all carried out at room temperature and normal pressure.

Example 1: Synthesis of ZIF-8

29.7 mg of zinc nitrate hexahydrate and 8 mg of 2-methylimidazole were accurately weighed into a 20 mL scintillation flask, added with 1 ml of N,N'-dimethylformamide, and then subjected to ultrasonic treatment until the ligand and the metal salt were dissolved completely, to obtain a clear solution, which was sealed with a sealing film. The sealed sample was irradiated under an electron accelerator for 1600 seconds, and then taken out, and the absorption dose was 1,000 kGy. The colorless crystals produced after irradiation were washed with absolute ethanol, and the finally obtained solid product was air-dried at room temperature.

Figure 1:
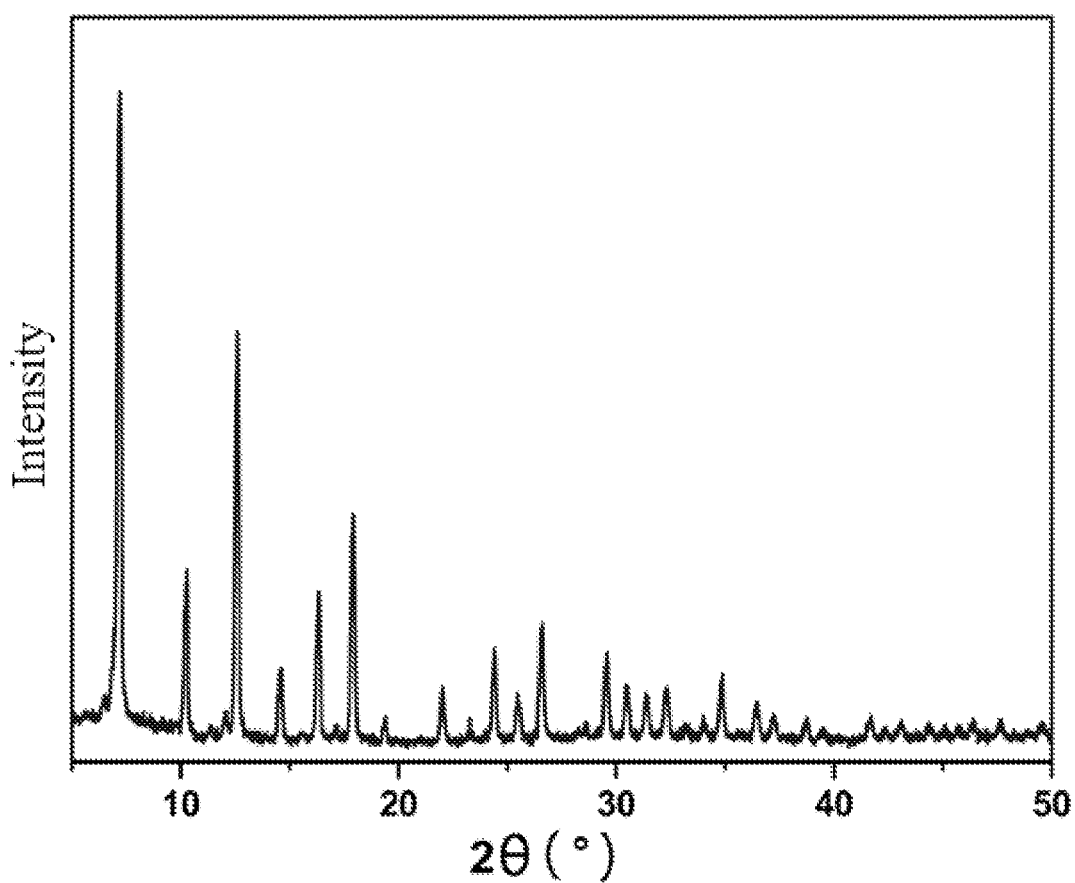
FIG. 1 shows the PXRD test result of ZIF-8 synthesized in Example 1 of the present invention.

The crystal structure of the product was tested by Powder X-ray Diffraction (PXRD), and the results are as shown in FIG. 1.

Example 2: Synthesis of UiO-66

128.9 mg of zirconium oxychloride octahydrate and 66.5 mg of terephthalic acid were accurately weighed into a 20 mL scintillation flask, added with 10 mL of N,N'-dimethylformamide, and then subjected to ultrasonic treatment until the ligand and the metal salt were dissolved completely, to obtain a clear solution, which was then added with 3 mL of acetic acid and sealed with a sealing film. The sealed sample was placed near and irradiated by a cobalt-60 source for 17 hours, and then taken out, and the absorption dose was 50 kGy. The irradiated white solid was washed twice with N,N'-dimethylformamide and twice with absolute ethanol, and the final product was air-dried at room temperature.

Figure 2:
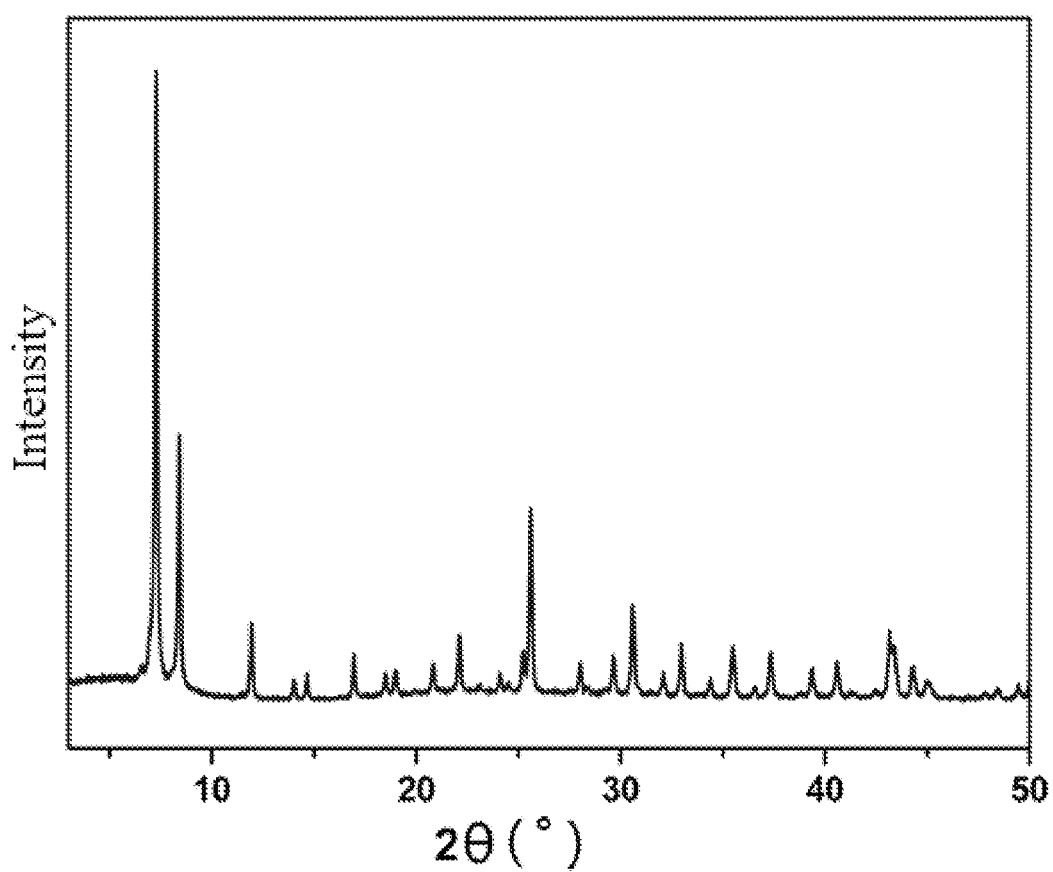
FIG. 2 shows the PXRD test result of UiO-66 synthesized in Example 2 of the present invention.

The crystal structure of the product was tested by Powder X-ray Diffraction (PXRD), and the results are as shown in FIG. 2.

Example 3: Synthesis of UiO-66

128.9 mg of zirconium oxychloride octahydrate and 66.5 mg of terephthalic acid were accurately weighed into a 20 mL scintillation flask, added with 10 mL of N,N'-dimethylformamide, and then subjected to ultrasonic treatment until the ligand and the metal salt were dissolved completely, to obtain a clear solution, which was then added with 3 mL of acetic acid and sealed with a sealing film. The sealed sample was placed near and irradiated by a cobalt-60 source for 17 hours, and then taken out, and the absorption dose was 100 kGy. The irradiated white solid was washed twice with N,N'-dimethylformamide and twice with absolute ethanol, and the final product was air-dried at room temperature.

Figure 3:
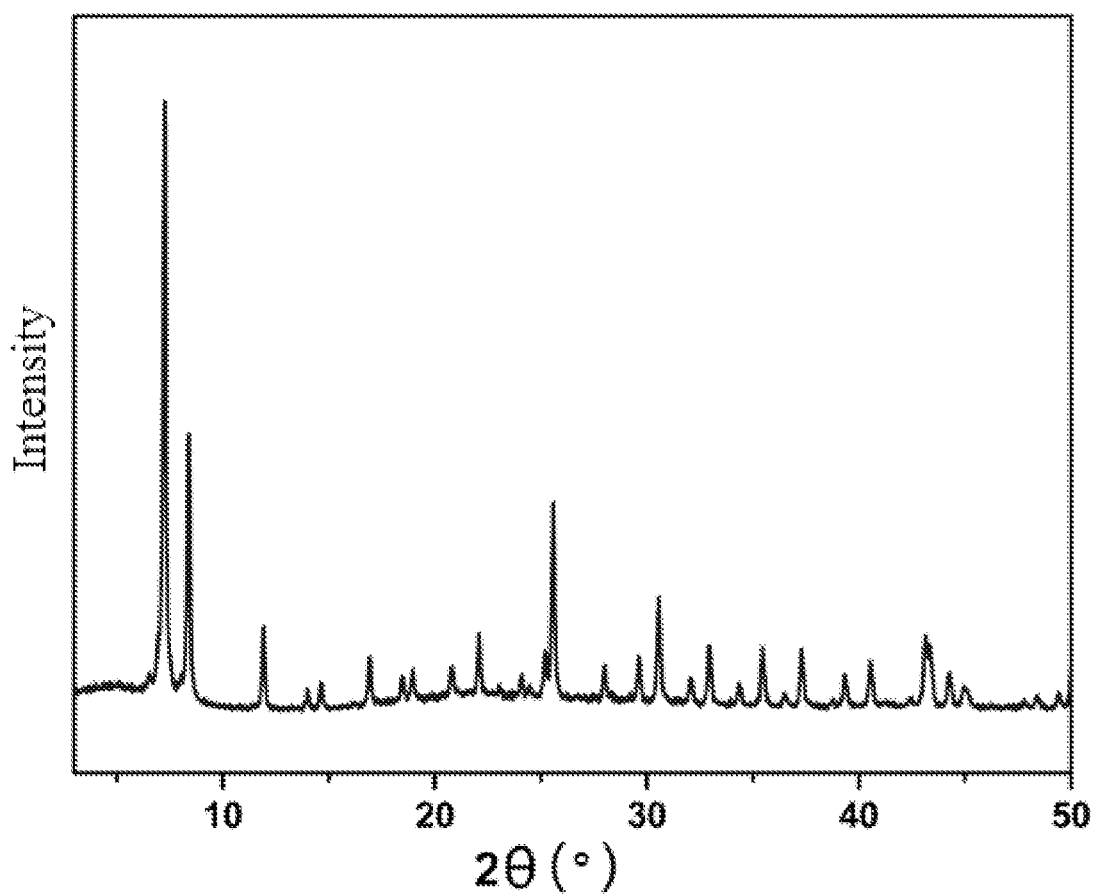
FIG. 3 shows the PXRD test result of UiO-66 synthesized in Example 3 of the present invention.

The crystal structure of the product was tested by Powder X-ray Diffraction (PXRD), and the results are as shown in FIG. 3.

Example 4: Synthesis of UiO-66

128.9 mg of zirconium oxychloride octahydrate and 66.5 mg of terephthalic acid were accurately weighed into a 20 mL scintillation flask, added with 10 mL of N,N'-dimethylformamide, and then subjected to ultrasonic treatment until the ligand and the metal salt were dissolved completely, to obtain a clear solution, which was then added with 3 mL of acetic acid and sealed with a sealing film. The sealed sample was placed near and irradiated by a cobalt-60 source for 17 hours, and then taken out, and the absorption dose was 200 kGy. The irradiated white solid was washed twice with N,N'-dimethylformamide and twice with absolute ethanol, and the final product was air-dried at room temperature.

Figure 4:
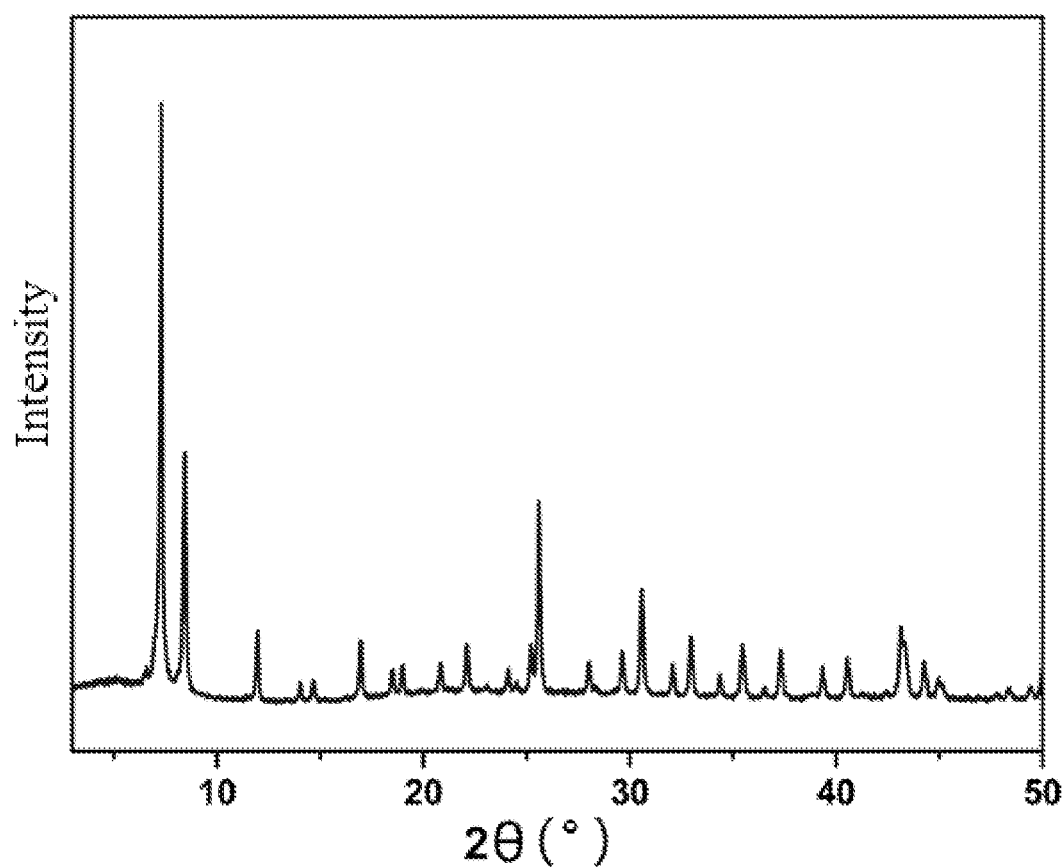
FIG. 4 shows the PXRD test result of UiO-66 synthesized in Example 4 of the present invention.

The crystal structure of the product was tested by Powder X-ray Diffraction (PXRD), and the results are as shown in FIG. 4.

Example 5: Synthesis of EB-COF-1

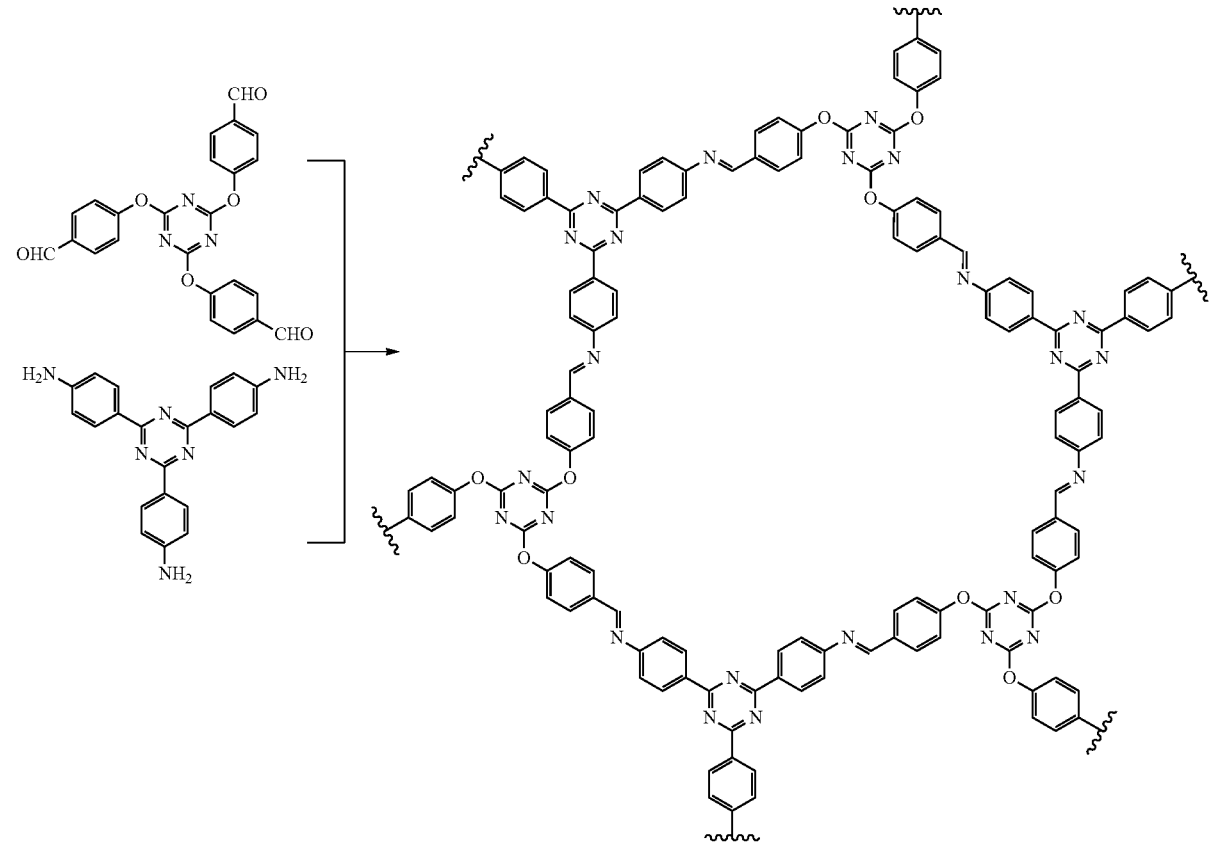 [SMILES: Nc1ccc(-c2nc(-c3ccc(N)cc3)nc(-c3ccc(N)cc3)n2)cc1 ; O=Cc1ccc(Oc2nc(Oc3ccc(C=O)cc3)nc(Oc3ccc(C=O)cc3)n2)cc1 ; *c1ccc(Oc2nc3nc(n2)Oc2ccc(cc2)/C=N/c2ccc(cc2)-c2nc(-c4ccc(*)cc4)nc(n2)-c2ccc(cc2)/N=C/c2ccc(cc2)Oc2nc(Oc4ccc(*)cc4)nc(n2)Oc2ccc(cc2)/C=N/c2ccc(cc2)-c2nc(-c4ccc(*)cc4)nc(n2)-c2ccc(cc2)/N=C/c2ccc(cc2)Oc2nc(Oc4ccc(*)cc4)nc(n2)Oc2ccc(cc2)/C=N/c2ccc(cc2)-c2nc(-c4ccc(*)cc4)nc(n2)-c2ccc(cc2)/N=C/c2ccc(cc2)O3)cc1]

88.3 mg of 2,4,6-tris(4-formylphenoxy)-1,3,5-triazine and 70.9 mg of 2,4,6-tris(4-aminophenyl)-1,3,5-triazine were accurately weighed into a 20 mL scintillation flask, added with 1 mL of n-butanol, 1 ml of 1,2-o-dichlorobenzene and 0.2 mL of a acetic acid solution (6 M), subjected to ultrasonic treatment for 1 min, then introduced with nitrogen for 4 min, and sealed. The sealed sample was irradiated under an electron accelerator for 160 seconds, and then taken out, and the absorption dose was 100 kGy. The yellow solid produced after irradiation was washed twice with tetrahydrofuran and once with absolute ethanol, and the finally obtained solid product was dried in a 60° C. oven.

Figure 5:
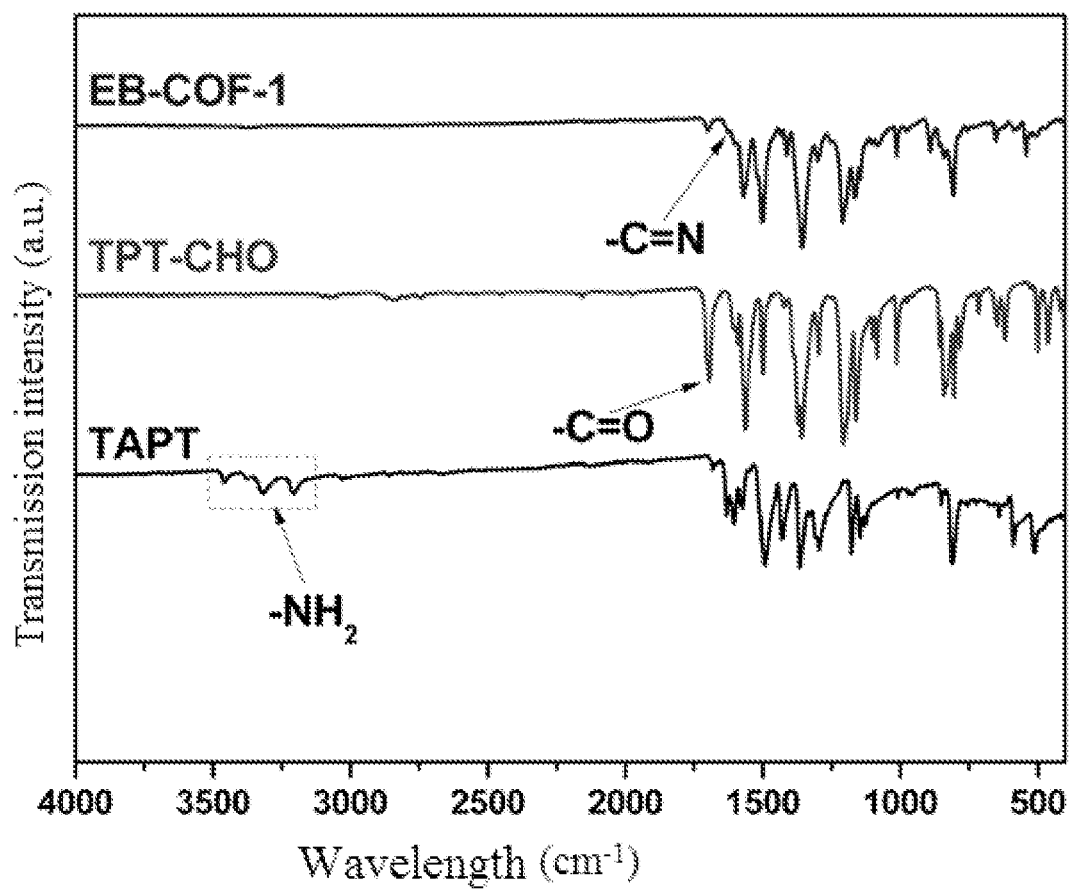
FIG. 5 shows the FT-IR test result of EB-COF-1 synthesized in Example 5 of the present invention.
Figure 6:
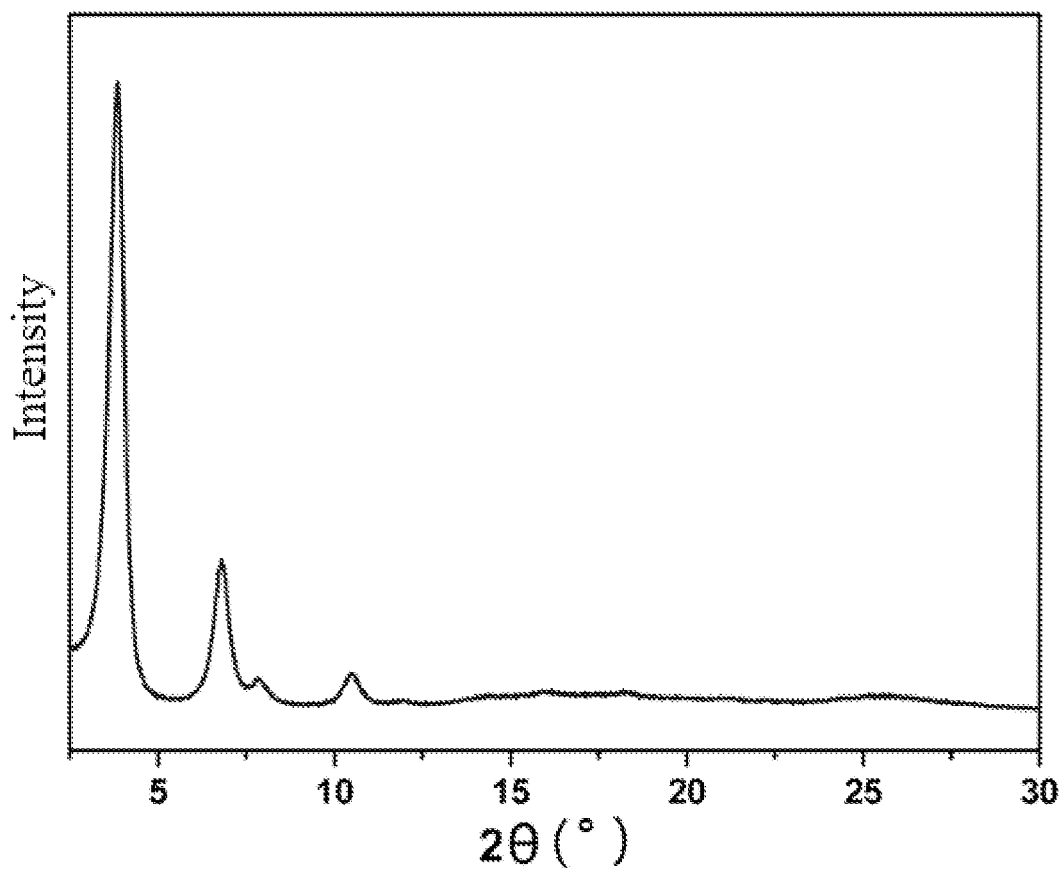
FIG. 6 shows the PXRD test result of EB-COF-1 synthesized in Example 5 of the present invention.

The chemical structure of the product was tested by a Fourier Transform Infrared Spectrometer (FT-IR). The results are as shown in FIG. 5. The crystal structure of the product was tested by Powder X-ray diffraction (PXRD). The results are as shown in FIG. 6.

Example 6: Synthesis of EB-COF-2

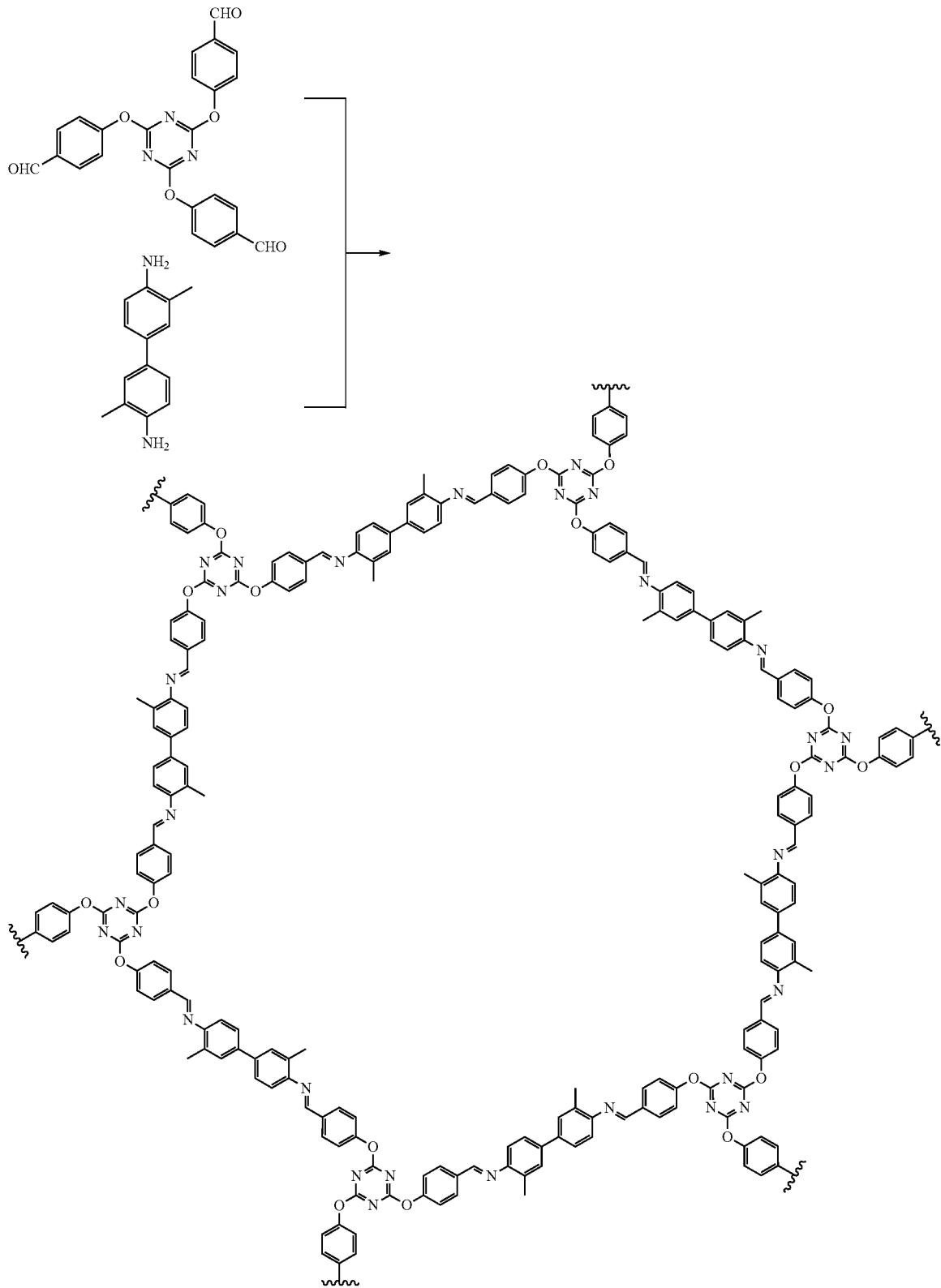

88.3 mg of 2,4,6-tris(4-formylphenoxy)-1,3,5-triazine and 3.7 mg of 3,3'-dimethylbenzidine were accurately weighed into a 20 mL scintillation flask, added with 1 mL of n-butanol, 1 ml of 1,2-o-dichlorobenzene and 0.2 mL of a acetic acid solution (6 M), subjected to ultrasonic treatment for 1 min, then introduced with nitrogen for 4 min, and sealed. The sealed sample was irradiated under an electron accelerator for 160 seconds, and then taken out, and the absorption dose was 100 kGy. The yellow solid produced after irradiation was washed twice with tetrahydrofuran and once with absolute ethanol, and the finally obtained solid product was dried in a 60° C. oven.

Figure 7:
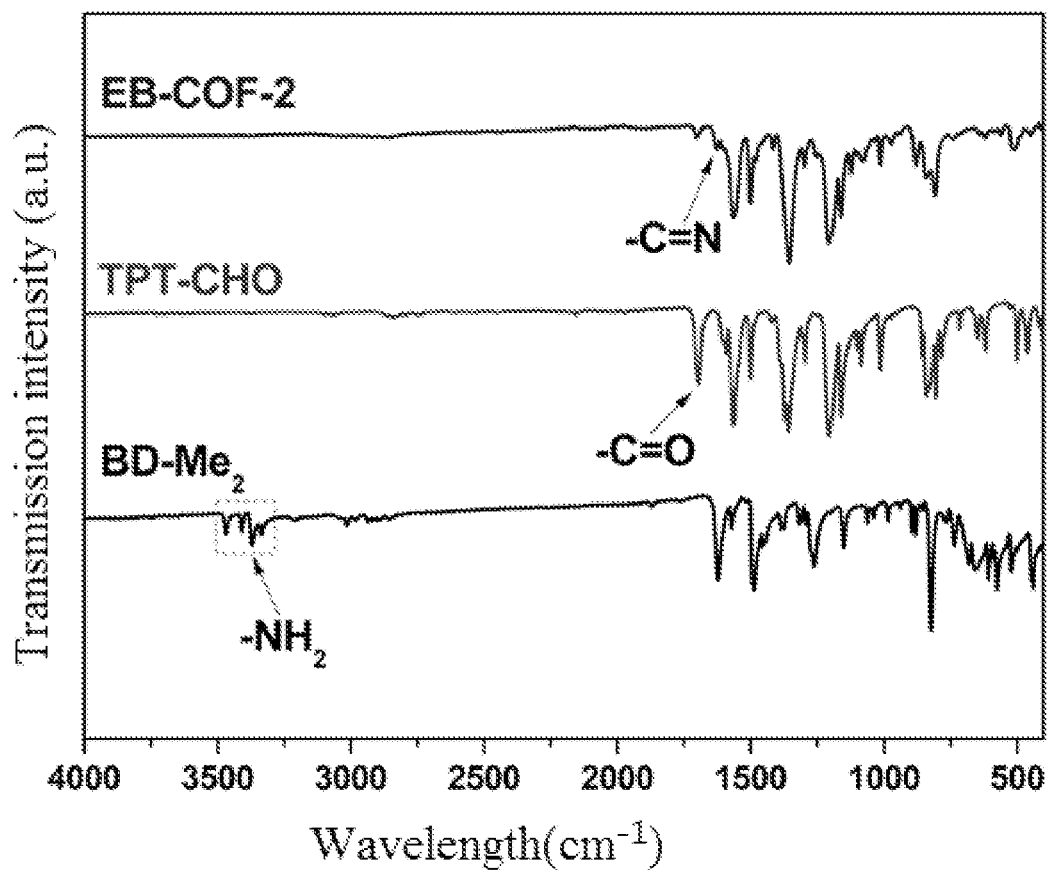
FIG. 7 shows the FT-IR test result of EB-COF-2 synthesized in Example 5 of the present invention.
Figure 8:
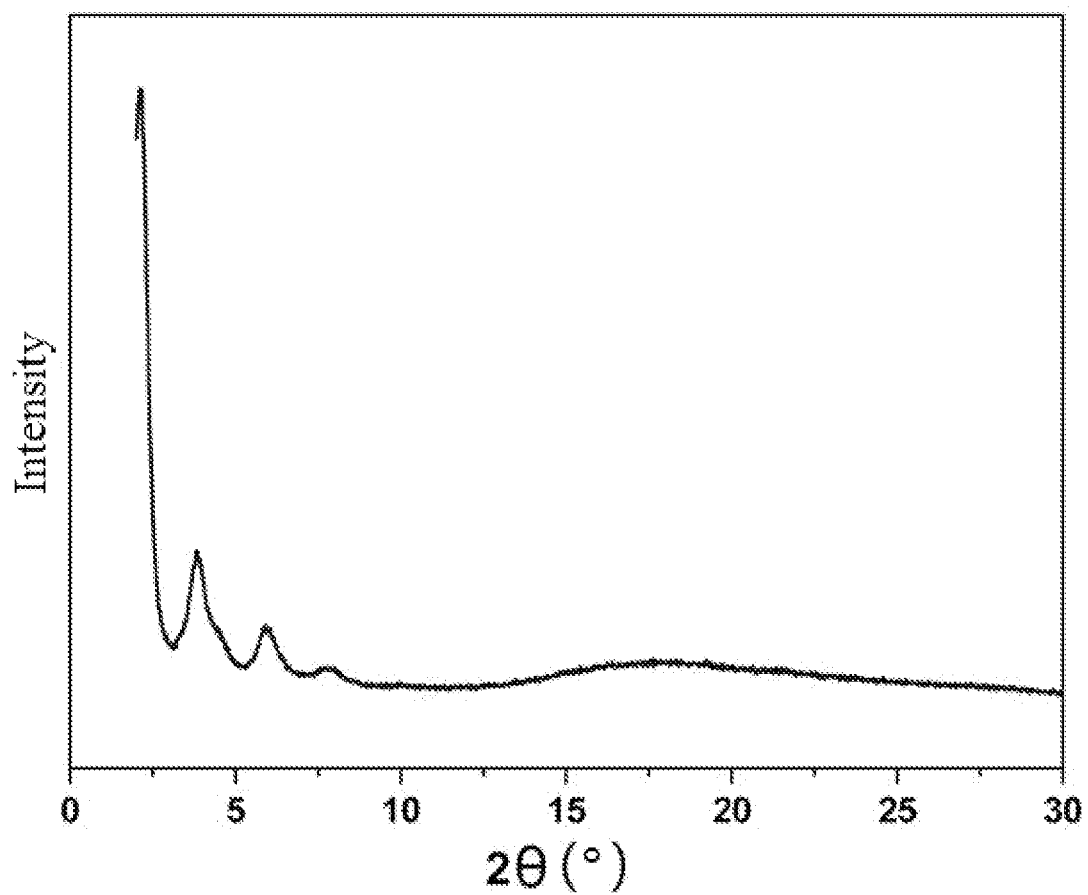
FIG. 8 shows the PXRD test result of EB-COF-2 synthesized in Example 5 of the present invention.

The chemical structure of the product was tested by a Fourier Transform Infrared Spectrometer (FT-IR), and the results are as shown in FIG. 7. The crystal structure of the product was tested by powder X-ray diffraction (PXRD), and the results are as shown in FIG. 8.

The present invention includes all novel porous crystalline materials (MOFs, COFs) prepared by ionizing radiation. The absorption dose involved in the present invention is not limited to 50, 100, 200 and 1,000 kGy mentioned herein, and other absorption doses suitable for synthesizing from raw materials are also included in the present invention. The ionization radiation source involved in the present invention is not limited to gamma rays and electron beams mentioned herein, and other ionization radiation sources suitable for synthesizing from raw materials are also included in the present invention. The organic solvents involved in the present invention are not limited to N,N'-dimethylformamide, n-butanol and 1,2-o-dichlorobenzene mentioned herein, and other organic solvents suitable for synthesizing from raw materials are also included in the present invention. The metal organic frameworks involved in the present invention is not limited to UiO-66 and ZIF-8 in the aforementioned examples, and other metal organic frameworks suitable for the present invention are also included in the present invention. The covalent organic frameworks involved in the present invention are not limited to EB-COF-1 and EB-COF-2 in the aforementioned examples, and other covalent organic frameworks suitable for the present invention are also included in the present invention.

The above are only the preferred embodiments of the present invention, and are not used for limiting the present invention. It should be noted that for those of ordinary skills in the art, various improvements and modifications may be made without departing from the principles of the present invention. These improvements and modifications should also be deemed as falling within the claimed scope of the present invention.

What is claimed is:

1. A method for synthesizing a porous crystalline material, comprising:
    irradiating a reaction mixture comprising a metal precursor and an organic ligand with an ionization radiation source at a temperature between 20° C. and 30° C. and normal pressure, wherein the ionization radiation source provides the energy required to synthesize a metal-organic framework (MOFs) or covalent-organic framework (COFs) material.

2. The method according to claim 1, wherein the ionization radiation source is selected from the group consisting of an electron beam, gamma-ray radiation, proton beam, helium ion beam and any combination thereof.

3. The method according to claim 1, wherein an irradiation dose of the ionization radiation source is 5-3,000 kGy; and the irradiation time of an ionization radiation source is 8 s-100 h.

4. The method according to claim 1, wherein the MOFs material comprises an inorganic metal center and an organic ligand connected with the inorganic metal center through a coordination bond, and the inorganic metal center is selected from transition metal ions, lanthanide metal ions, actinide metal ions and any combination thereof; and the organic ligand is derived from imidazole, carboxylic acid or pyridine ligands.

5. The method according to claim 1, wherein the COFs material comprises a light element and an organic structural unit connected with the light element through a covalent bond, wherein the light element is selected from C, H, B, O, N atoms and any combination thereof, and the organic structural unit is a conjugated structural unit.

6. A method for preparing a metal-organic framework MOFs material, comprising steps of:
    dissolving a metal salt and an organic ligand in an organic solvent to form a reaction mixture; and then irradiating the reaction mixture with an ionization radiation source at a temperature between 20° C. and 30° C. under and normal pressure for a time sufficient to complete the synthesis of the MOFs material, wherein the ionization radiation source provides the energy required for the reaction to occur without the need for external heating.

7. The method according to claim 6, wherein the ionization radiation source has an irradiation dose of 5-3,000 kGy and an irradiation time of 8 s-100 h.

8. The method according to claim 6, wherein the organic solvent is selected from N,N-dimethylformamide (DMF), n-butanol, or 1,2-o-dichlorobenzene.

9. The method according to claim 6, wherein the metal salt is selected from the group consisting of zinc salts, zirconium salts, copper salts, cobalt salts, lanthanide metal salts, and actinide metal salts.

10. The method according to claim 6, wherein the irradiation dose of the ionization radiation source is between 50 kGy and 1,000 kGy.

11. The method according to claim 6, wherein the irradiation time of the ionization radiation source is less than 17 hours.

12. The method according to claim 6, wherein the MOFs material is selected from the group consisting of ZIF-8 and UiO-66.

13. The method according to claim 6, wherein the ionization radiation source is selected from the group consisting of gamma-ray radiation, electron beam radiation, and proton beam radiation.

14. The method according to claim 6, wherein the reaction mixture is subjected to sonication before irradiation.

15. The method according to claim 6, wherein the organic ligand is derived from imidazole, carboxylic acid, or pyridine ligands.

16. The method according to claim 6, further comprising purging the reaction mixture with an inert gas before irradiating.

17. The method according to claim 6, wherein the irradiated reaction mixture is washed with an organic solvent selected from ethanol or tetrahydrofuran after irradiation.

18. The method according to claim 6, wherein the metal-organic framework material is used for gas storage, separation, or catalysis applications.

19. The method according to claim 6, wherein the irradiated reaction mixture is dried at room temperature after washing to obtain the final MOFs material.

* * * * *